United States Patent
Koppe

(10) Patent No.: US 11,931,272 B2
(45) Date of Patent: Mar. 19, 2024

(54) ORTHOPEDIC DEVICE AND CONDUCTOR FOR SUCH A DEVICE

(71) Applicant: Ottobock SE & Co. KGaA, Duderstadt (DE)

(72) Inventor: Mario Koppe, Göttingen (DE)

(73) Assignee: OTTOBOCK SE & CO. KGAA, Duderstadt (DE)

( * ) Notice: Subject to any disclaimer, the term of this patent is extended or adjusted under 35 U.S.C. 154(b) by 0 days.

(21) Appl. No.: 15/733,053

(22) PCT Filed: Oct. 16, 2018

(86) PCT No.: PCT/EP2018/078232
§ 371 (c)(1),
(2) Date: Apr. 30, 2020

(87) PCT Pub. No.: WO2019/091713
PCT Pub. Date: May 16, 2019

(65) Prior Publication Data
US 2020/0289295 A1  Sep. 17, 2020

(30) Foreign Application Priority Data
Nov. 10, 2017 (DE) .................. 10 2017 126 465.5

(51) Int. Cl.
*A61F 2/70* (2006.01)
*A61F 2/50* (2006.01)
(Continued)

(52) U.S. Cl.
CPC .............. *A61F 2/70* (2013.01); *A61F 2/5044* (2013.01); *A61F 2/72* (2013.01);
(Continued)

(58) Field of Classification Search
CPC .................................................. A61F 2/7812
See application file for complete search history.

(56) References Cited

U.S. PATENT DOCUMENTS

| 4,092,985 A | 6/1978 | Kaufman |
| 2006/0111792 A1* | 5/2006 | Shannon ............... A61F 2/7812 623/36 |

(Continued)

FOREIGN PATENT DOCUMENTS

| CN | 201004344 Y | 1/2008 |
| CN | 101548576 A | 9/2009 |

(Continued)

OTHER PUBLICATIONS

Chou et al., "Deposition, characterization, and in vivo performance of parylene coating on general-purpose silicone for examining potential biocompatible surface modifications," Thin Solid Films 549, 2013, pp. 103-107, 6 pages.

(Continued)

*Primary Examiner* — Jacqueline Woznicki
(74) *Attorney, Agent, or Firm* — HOLLAND & HART LLP

(57) ABSTRACT

An orthopedic device with a base body made of an electrically insulating material and at least one electric conductor which is arranged on or in the base body. The at least one conductor comprises a core made of an electrically conductive elastomer and an electrically insulating coating.

15 Claims, 5 Drawing Sheets

(51) Int. Cl.
*A61F 2/72* (2006.01)
*A61F 2/76* (2006.01)
*A61F 2/78* (2006.01)
*A61F 2/80* (2006.01)

(52) U.S. Cl.
CPC ..... *A61F 2002/7615* (2013.01); *A61F 2/7812* (2013.01); *A61F 2/80* (2013.01)

(56) References Cited

U.S. PATENT DOCUMENTS

| | | |
|---|---|---|
| 2009/0216339 A1 | 8/2009 | Hanson et al. |
| 2009/0255706 A1 | 10/2009 | Jiang et al. |
| 2010/0044075 A1 | 2/2010 | Weiss et al. |
| 2010/0114238 A1 | 5/2010 | Muccio |
| 2013/0046394 A1 | 2/2013 | Lipschutz et al. |
| 2013/0166009 A1* | 6/2013 | Branemark ............ A61F 2/2814 607/149 |
| 2014/0188251 A1* | 7/2014 | Mosler ............... A61N 1/36003 623/33 |
| 2015/0257315 A1 | 9/2015 | Wagner et al. |
| 2016/0038314 A1* | 2/2016 | Kuiken ................... A61F 2/76 623/36 |
| 2017/0333223 A1* | 11/2017 | Rasmussen ............... A61F 2/80 |
| 2018/0296822 A1* | 10/2018 | Schroeder ............. A61L 31/126 |
| 2018/0297214 A1* | 10/2018 | Lessing .................... A61H 3/00 |
| 2019/0167976 A1* | 6/2019 | Byers .................... A61N 1/0452 |
| 2019/0254845 A1* | 8/2019 | Wernke ...................... A61F 2/72 |
| 2020/0289295 A1* | 9/2020 | Koppe ....................... A61F 2/70 |
| 2022/0031480 A1* | 2/2022 | Bause .................... B29C 64/106 |

FOREIGN PATENT DOCUMENTS

| | | |
|---|---|---|
| CN | 101556839 A | 10/2009 |
| CN | 103702638 A | 4/2014 |
| CN | 104684477 A | 6/2015 |
| DE | 102014106070 A1 | 11/2012 |
| DE | 102011101583 | 11/2015 |
| EP | 2737878 A1 | 6/2014 |
| WO | WO2014052080 A1 | 4/2014 |

OTHER PUBLICATIONS

"International Search Report and Written Opinion of the International Searching Authority," issued in connection with Int'l Appl. No. PCT/EP2018/078232, dated Dec. 20, 2018 (19 pages).

Chinese Patent Office, "Search report," issued in connection with Chinese Patent Application No. 201880071957.1 dated Nov. 22, 2022 (2 pages).

\* cited by examiner

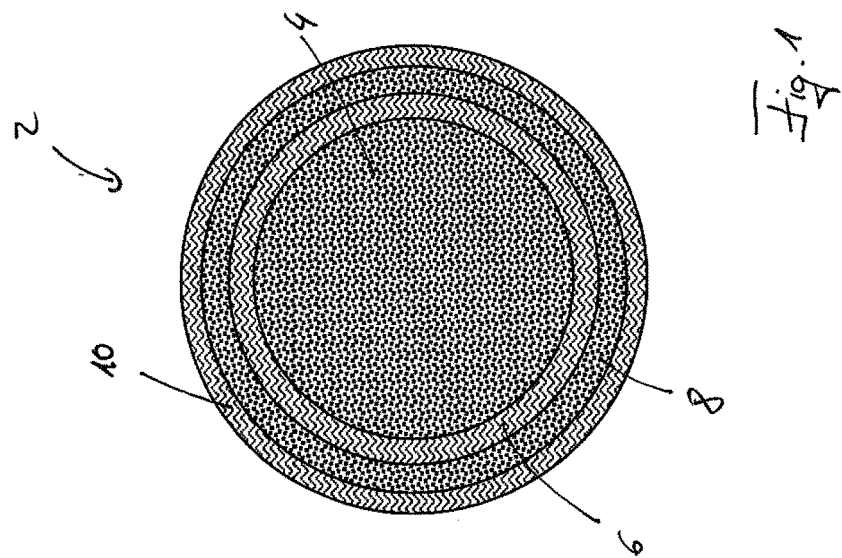
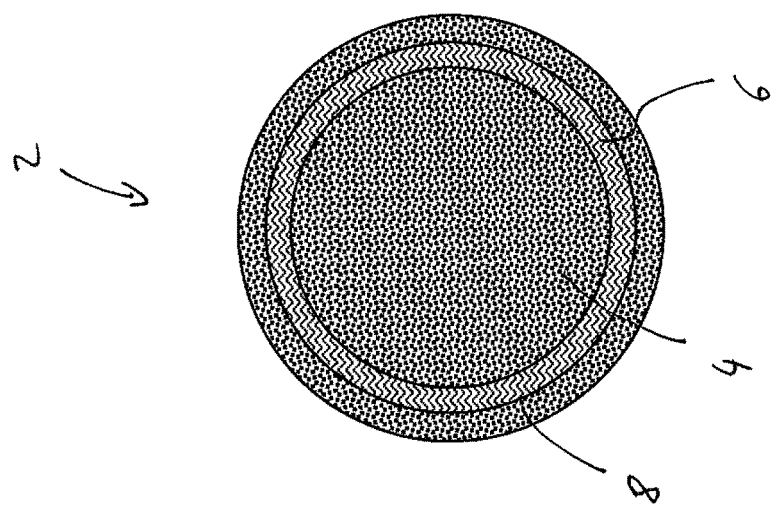
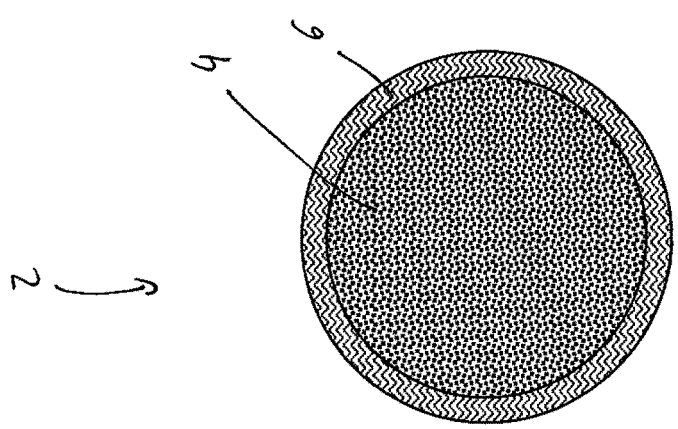
Fig. 1

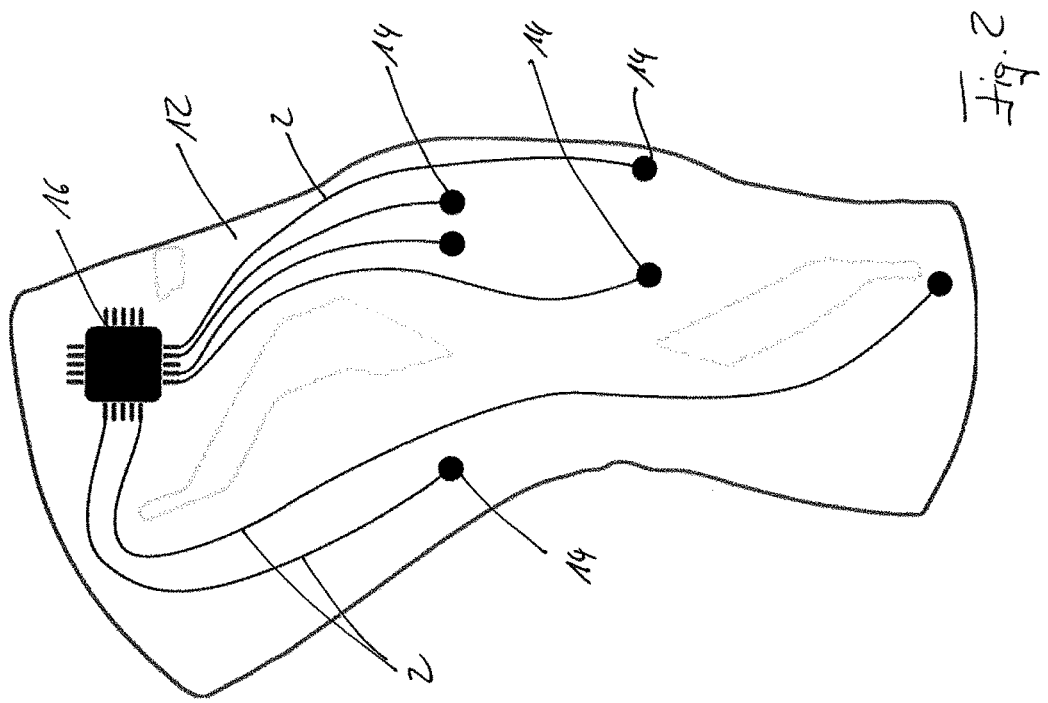

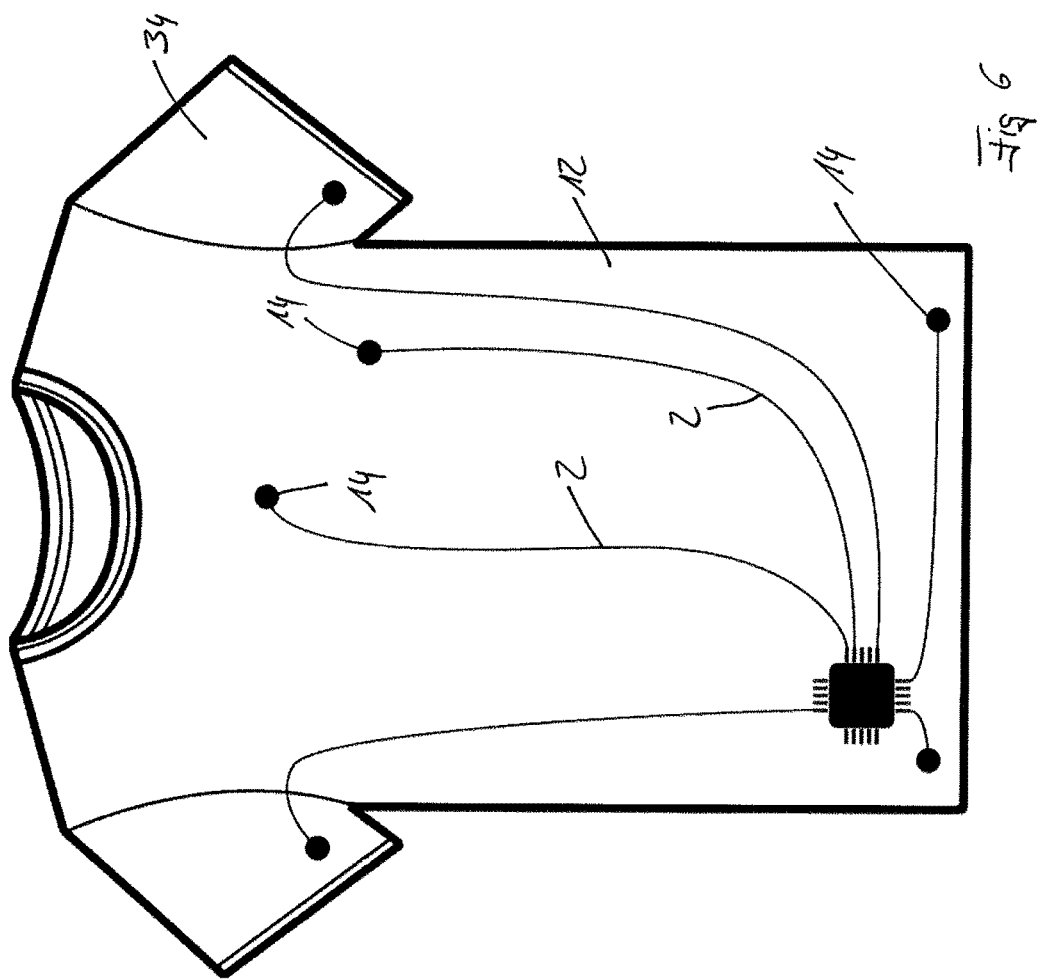

ORTHOPEDIC DEVICE AND CONDUCTOR FOR SUCH A DEVICE

CROSS REFERENCE TO RELATED APPLICATIONS

This application is a U.S. National Entry and claims priority to PCT International Patent Application No. PCT/EP2018/078232, filed 16 Oct. 2018, and entitled "ORTHOPEDIC DEVICE AND CONDUCTOR FOR SUCH A DEVICE", which claims priority to Germany Patent Application No. 10 2017 126 465.5 filed 10 Nov. 2017, the entire disclosures of which are incorporated herein by this reference.

TECHNICAL FIELD

The invention relates to an orthopedic device with a base body made of an electrically insulating material and at least one electric conductor which is arranged on or in the base body. The invention also relates to a conductor for such an orthopedic device and a method for producing such a conductor.

BACKGROUND

Within the scope of the present invention, orthopedic devices are specifically orthoses, prostheses, especially prosthesis sockets and prosthesis liners, or other rehabilitation devices. Nowadays, orthopedic devices are often equipped with electrodes in order to pick up and transmit myoelectric signals to a data processing device or to conduct electric stimulation signals to the skin and/or an underlying muscle thereof of the patient, i.e. the wearer of the orthopedic device. This is particularly advantageous in the case of the prosthesis liners, as they come into direct contact with the skin of the wearer and are thus especially well-suited to bear corresponding electrodes. Of course, the present invention is not limited to prosthesis liners.

A series of different electrodes is known from the prior art, wherein said series of electrodes can be brought into contact with the skin of the wearer of the orthopedic device. These may be arranged, for instance, on the inner side of the orthopedic device, such as the prosthesis liner, i.e. in direct contact with the skin, or positioned on the outer side of the liner, for example on the inner side of a prosthesis socket surrounding the liner. In this case, the liner often has electrically conductive through-lines, for instance in the form of metal rivets, or electrically conductive silicone areas, such that the orthopedic device has been rendered electrically conductive in the area around the electrodes.

However, it is disadvantageous that in this case the electrodes must be arranged precisely at the point at which the through-lines are arranged in the orthopedic device as well as precisely at the point at which they must be arranged on the wearer, for example on an amputation stump. These electrodes, which often require a lot of space, can therefore often not be arranged at the optimum point.

The prior art thus describes a series of different possibilities for arranging electrical conductors in or on the base body made of electrically insulating material. For instance, it is known to use silver fabric to conduct electric signals through the base body of the orthopedic device to a further processing point, such as an electronic data processing device. However, the disadvantage of using silver is that it is highly susceptible to corrosion; it also does not possess sufficient elasticity. This is especially disadvantageous if the conductor produced in such a manner is arranged in an orthopedic device which itself is made of an elastic material.

Therefore, DE 10 2014 106 070 A1 describes a method in which a prosthesis liner is equipped with electrically conductive conductors. First, the base body is produced from an electrically insulating elastomer material. Said material is crosslinked. Structures are then inserted into the first formed elastomer material; said structures serve as a mould for the electrical cables. A second elastomer material is subsequently inserted into these structures and then cross-linked, said material being electrically conductive. In this way, an electric conductor is produced from an electrically conductive elastomer material; said conductor is arranged in recesses in the base body.

However, it is disadvantageous that this method only allows for the arrangement of electrically conductive structures in a surface of the base body, and that it is complex and therefore time-consuming and expensive.

The invention therefore aims to further develop an orthopedic device according to the generic term in claim 1 in such a way that electric conductors can be arranged especially easily in or on the base body and elastic properties of the base body are not adversely affected.

SUMMARY

The invention solves the problem by way of an orthopedic device according to the present disclosure, wherein the at least one conductor comprises a core made of an electrically conductive elastomer and an electrically insulating coating.

This type of conductor may be provided in the form of a cable or cord, for example. The elastomer of the core may be rendered electrically conductive through the addition of particles, for instance. A coating made of electrically insulating material is applied to core shaped in this manner, for example in the form of the aforementioned cord or cable. Here, the coating preferably does not have an adverse effect on the elastic and flexible properties of the core, so that they correspond to the elastic and flexible properties of the electric conductor. This conductor can now be easily arranged in or on the base body of the orthopedic device; for example, it can be cast into an elastomer material of a prosthesis liner. In this case, as both the core of the electric conductor and the electrically insulating material of the base body are elastomers, elastic properties of the orthopedic device are also not adversely affected.

Preferably, an elastomer of the core is a silicone, a thermoplastic elastomer or a polyurethane, in which graphite, soot and/or metal particles and/or carbon nanotubes are found. Alternatively or additionally, conductive fibers may also be used.

The electrically insulating coating preferably contains or is made from a parylene. The use of parylene as an insluting coating has the additional advantage that it also functions as a bonding agent; this is particularly true when both the electrically insulating material of the base body and the electrically conductive elastomer of the conductor are a polyurethane or a silicone. The parylene coating not only enables an electrically insulating effect to be achieved, but it also ensures an effective bond between the material of the base body of the orthopedic device and the electric conductor.

The material of the base body preferably contains or is made of a silicone, a thermoplastic elastomer or a polyurethane.

Preferably, the orthopedic device comprises at least one electrode and/or at least one sensor, wherein the electrode and/or the sensor is electrically connected to the at least one conductor and is preferably arranged such that, when the device is mounted on a body part, it comes into contact with that body part. This enables a particularly effective contact for transmitting electrical signals and impulses; at the same time, it ensures that, even when the orthopedic device is subjected to high mechanical and/or thermal loads, a reliable transmission of the signals is guaranteed. The at least one sensor preferably features a pressure sensor, a temperature and/or moisture sensor, a pulse measurement and/or blood circulation measurement sensor (N IRS) and/or a sensor for measuring blood glucose levels.

Rather than arrange the electrodes and/or sensors on the skin of the wearer of the orthopedic device, a distance to the skin may be maintained if the electrode and/or the sensor works in a capacitive or inductive manner.

Preferably, the at least one conductor features a shielding made of an electrically conductive elastomer that is arranged on the side of the insulating coating that faces away from the core. The electric conductor is thus constructed in three layers from radially inwards to radially outwards and initially has a core of electrically conductive material, preferably an elastomer, which is covered by the electrically insulating coating on whose outer side the shielding is situated. It is thereby possible to produce a type of electric conductor shielded with a coaxial cable that does not have an adverse effect on the elastic and flexible properties, especially of a prosthesis liner.

The shielding preferably comprises or is made of the same material as the core of the electric conductor.

The invention also solves the task by way of a conductor for a prosthesis as described here. The invention also solves the task by way of a method for producing such a conductor, wherein the coating is produced by a CVD process. The abbreviation CVD stands for "chemical vapour deposition" and describes a chemical coating process that experts know from the prior art.

In the following, an example of an embodiment of the present invention will be explained in more detail by way of the attached figures:

BRIEF DESCRIPTION OF THE DRAWINGS

FIG. 1—schematic sectional view through a conductor for an orthopedic device according to a first example of an embodiment of the present invention and FIGS. 2 to 6—different orthopedic devices according to further examples of an embodiment of the present invention.

DETAILED DESCRIPTION

Figure 4:
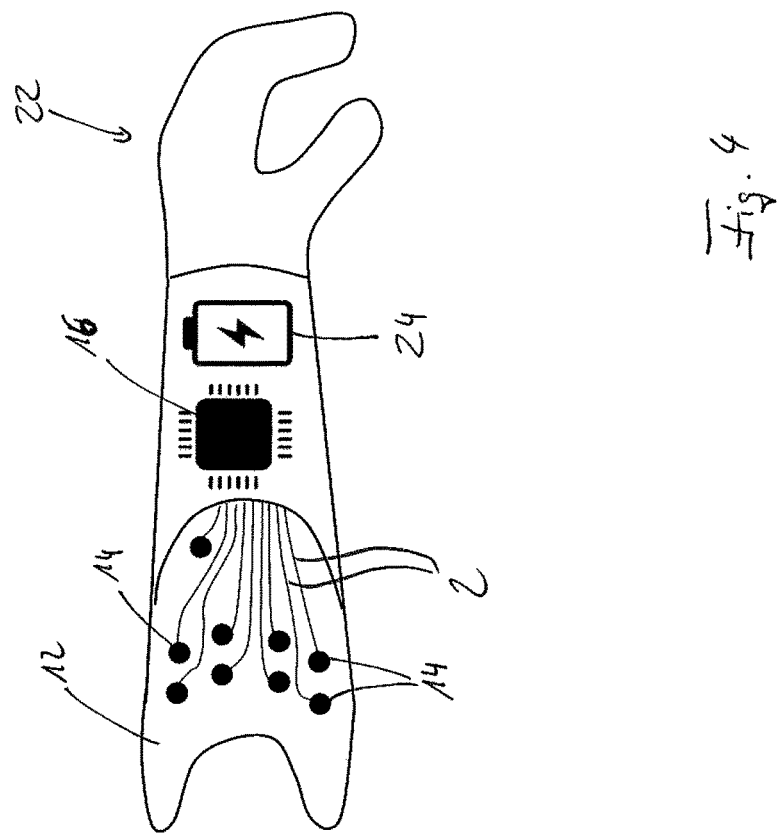

In the left-hand representation, FIG. 1 depicts a cut through an electric conductor 2 for an orthopedic device according to a first example of an embodiment of the present invention. The electric conductor 2 comprises a core 4 made of an electrically conductive elastomer, such as a silicone mixed with graphite particles. The core 4 is surrounded by a coating 6, which is made of an electrically insulating material, such as parylene.

The central representation in FIG. 1 shows an electric conductor 2, where the core 4 with the surrounding coating 6 is surrounded by a shielding 8, which is also made of an electrically conductive elastomer and arranged on the side of the insulating coating 6 that faces away from the core 4. This renders it possible to produce an electric conductor 2 which has the properties of a coaxial cable with an electrical shielding 8.

The right-hand representation in FIG. 1 shows an electric conductor 2 with a shielding 8, like in the central representation; however, said shielding is now surrounded by a second coating 10. As is the case with the coating 6, the second coating 10 is an electrically insulating coating which is preferably made of the same material as the coating 6.

FIG. 2 depicts an orthopedic device in the form of a knee support. It has a base body 12, which can be made, for instance, of an elastic textile and may feature thickenings, pads or inserted or integrated padding elements. In the example of an embodiment shown, six electrodes/sensors 14 are integrated in the base body 12, each of which is connected to an electric conductor 2. The electric conductors 2 connect the electrodes/sensors 14 to an electric control system 16, which is depicted schematically in FIG. 2. The electric control system 16 is configured to further process electrical signals that are sent by the electrodes/sensors 14 via the electric conductor 2 to the electric control system 16 and, where applicable, to transfer them to an electronic data processing device. For example, this may occur via cables, not depicted in FIG. 2, which is especially advantageous if the electronic data processing device is arranged in the electric control system 14 or at least on the base body 12 of the orthopedic device. It may be practical, for instance, to further develop the electrical signals transmitted by the electrodes/sensors 14 in the form of electronic data in the electric control system in such a way that they can be stored in an electronic memory, which is preferably part of the orthopedic device, until they can be read and evaluated. Alternatively, or additionally, it is beneficial to allow for a wireless transmission of the electronic data from the electric control system 16 to an electronic data processing device.

Figure 3:
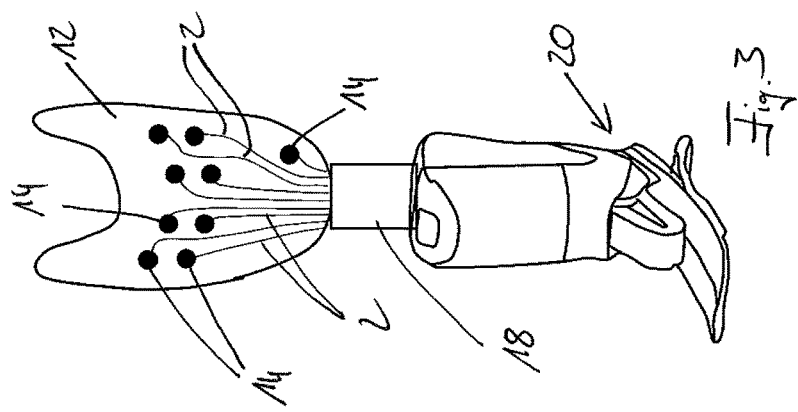

FIG. 3 shows an orthopedic device according to a further example of an embodiment of the present invention in the form of a lower leg prosthesis. The base body 12 is designed in the form of a prosthesis socket on which the electrodes/sensors 14 are arranged; these are connected to an electric control system via electric conductors 2, wherein said electric control system is not depicted. A lower leg element 18 and an artificial foot 20 are situated on the base body 12. Via the electrodes/sensors 14, myoelectric signals, for instance, can be picked up from an amputation stump that is arranged in the base body 12. These myoelectric signals are directed to the electric control system via the electric conductors 2 and used to control the artificial foot 18.

FIG. 4 depicts another embodiment of an orthopedic device according to an example of an embodiment of the present invention, which is also designed as a prosthesis; however, here it is designed as a hand or lower arm prosthesis. Here, the base body 12 also forms a prosthesis socket on which the electrodes/sensors 14 are arranged; these are connected to the electric control system 16 via electric conductors. The electric control system 16 is configured to generate control signals for a prosthetic hand 22 using the electrical signals picked up by the electrodes/sensors 14 and to thereby control the functions of the prosthetic hand 22. The orthopedic device shown in FIG. 4 also features a power supply 24 by means of which the electric control system 16 can be supplied with electrical energy.

Figure 5:
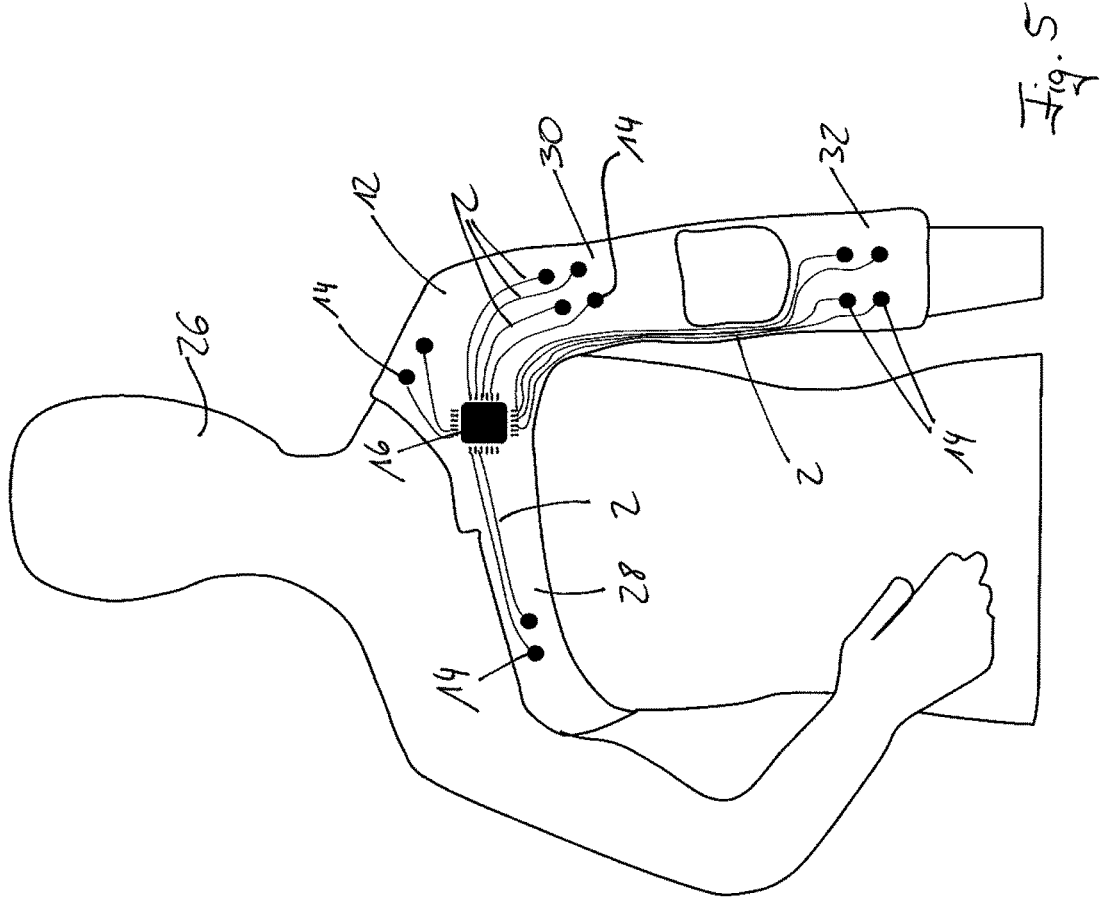

FIG. 5 depicts an embodiment of an orthopedic device which is designed as a shoulder orthosis. The base body 12 extends across the shoulder region of the wearer 26, along the arm of the wearer 26 and over the elbow. The base body 12 has a fixing belt 28, which is guided around the torso of the wearer 24. Electrodes/sensors 14 are arranged on both the fixing belt 28, which forms part of the base body 12, and on other parts of the base body 12, such as an upper arm element 30 and a lower arm element 32; said electrodes/sensors are connected to the electric control system 16 via electric conductors 2.

FIG. 6 depicts an orthopedic device in the form of a t-shirt, wherein the base body 12 is the t-shirt itself. Electrodes/sensors 14 are arranged on both the sleeves 34 and the rest of the base body 12, wherein said electrodes/sensors are connected to the electric control system 16 via electric conductors 2. The difficulty with this configuration of the orthopedic device is establishing as effective a contact as possible between the electrodes/sensors 14 and the skin area of the wearer 24. This may be achieved, for instance, by way of the cut of the t-shirt, an elastic material or integrated belts.

I claim:

1. An orthopedic device comprising:
   a base body made of an electrically insulating material comprising at least one of a silicone, a thermoplastic elastomer, or a polyurethane;
   at least one electrode/sensor arranged within the base body such that, when the orthopedic device is mounted on a body part, the at least one electrode/sensor comes into contact with that body part; and
   at least one electric conductor arranged within the base body and connected to the at least one electrode/sensor, the at least one conductor comprising a core made of an electrically conductive elastomer and an electrically insulating coating surrounding the core, wherein the at least one electrical conductor is arranged in the base body by casting the at least one electrical conductor into the base body, wherein the electrically insulating coating comprises poly(p-xylylene) polymers and derivates thereof.

2. The orthopedic device according to claim 1, wherein the elastomer is a silicone, a thermoplastic elastomer or a polyurethane, in which at least one of graphite, soot and at least one of metal particles and carbon nanotubes are found.

3. The orthopedic device according to claim 1, wherein the material of the base body comprises the thermoplastic elastomer or the polyurethane.

4. The orthopedic device according to claim 1, wherein the device at least one electrode/sensor comprises at least one sensor, wherein the at least one sensor is electrically connected to the at least one conductor and is arranged such that, when the device is mounted on a body part, the device comes into contact with that body part.

5. The orthopedic device according to claim 1, wherein the at least one conductor comprises a shielding made of an electrically conductive elastic material, which is arranged on a side of the insulating coating that faces away from the core.

6. The orthopedic device according to claim 5, wherein the shielding comprises the same material as the core.

7. A conductor for an orthopedic device according to claim 1.

8. A method for producing a conductor according to claim 7, wherein the coating is produced by a CVD procedure.

9. An orthopedic device comprising:
   a base body comprising an electrically insulating material comprising at least one of silicone, a thermoplastic elastomer, or a polyurethane;
   at least one electrode/sensor arranged within the base body such that, when the orthopedic device is mounted on a body part, the at least one electrode/sensor comes into contact with that body part; and
   at least one electric conductor arranged within the base body and connected to the at least one electrode/sensor, the at least one conductor comprising:
   a core comprising an electrically conductive elastomer; and
   an electrically insulating coating surrounding the core, wherein the at least one electrical conductor is arranged in the base body by casting the at least one electrical conductor into the base body, wherein the electrically insulating coating comprises poly(p-xylylene) polymers and derivates thereof.

10. The orthopedic device according to claim 9, wherein the elastomer is the silicone, the thermoplastic elastomer or the polyurethane, in which at least one of graphite, soot and at least one of metal particles and carbon nanotubes are found.

11. The orthopedic device according to claim 9, wherein the material of the base body comprises the thermoplastic elastomer or the polyurethane.

12. The orthopedic device according to claim 9, wherein the at least one electrode/sensor comprises at least one sensor, and the sensor is electrically connected to the at least one conductor and is arranged such that, when the device is mounted on a body part, the device comes into contact with that body part.

13. The orthopedic device according to claim 9, wherein the at least one conductor comprises a shielding made of an electrically conductive elastic material, which is arranged on a side of the insulating coating that faces away from the core.

14. The orthopedic device according to claim 13, wherein the electrically conductive elastic material comprises an elastomer.

15. The orthopedic device according to claim 9, wherein the shielding comprises the same material as the core.

* * * * *